United States Patent
Schleicher et al.

(10) Patent No.: US 8,666,493 B2
(45) Date of Patent: *Mar. 4, 2014

(54) FIXATION OF IMPLANTABLE PULSE GENERATORS

(71) Applicant: Boston Scientific Neuromodulation Corporation, Valencia, CA (US)

(72) Inventors: Brett Daniel Schleicher, Valencia, CA (US); Todd K. Whitehurst, Frederick, MD (US); Andrew DiGiore, San Francisco, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,735

(22) Filed: Jan. 28, 2013

(65) Prior Publication Data

US 2013/0184790 A1 Jul. 18, 2013

Related U.S. Application Data

(63) Continuation of application No. 12/361,432, filed on Jan. 28, 2009, now Pat. No. 8,364,267.

(60) Provisional application No. 61/024,115, filed on Jan. 28, 2008.

(51) Int. Cl.
*A61N 1/00* (2006.01)

(52) U.S. Cl.
USPC .............................................. 607/36; 607/2

(58) Field of Classification Search
USPC ........................................................ 607/2, 36
See application file for complete search history.

(56) References Cited

U.S. PATENT DOCUMENTS

| 4,519,404 | A | * | 5/1985 | Fleischhacker | ............... 607/126 |
|---|---|---|---|---|---|
| 5,431,681 | A | | 7/1995 | Helland | |
| 5,476,500 | A | | 12/1995 | Fain et al. | |
| 5,571,163 | A | | 11/1996 | Helland | |
| 5,693,081 | A | | 12/1997 | Fain et al. | |

(Continued)

FOREIGN PATENT DOCUMENTS

| WO | 9508366 A1 | 3/1995 |
|---|---|---|
| WO | 9808554 A1 | 3/1998 |

(Continued)

OTHER PUBLICATIONS

U.S. Appl. No. 12/361,432 Official Communication mailed Oct. 4, 2011.

(Continued)

*Primary Examiner* — Niketa Patel
*Assistant Examiner* — William Levicky
(74) *Attorney, Agent, or Firm* — Frommer Lawrence & Haug LLP; Bruce E. Black

(57) ABSTRACT

Systems and techniques for improving the fixation of implantable pulse generators. In one aspect, a device includes an implantable pulse generator that comprises electrical circuitry configured to generate an electrical pulse and a biocompatible casing that houses the electrical circuitry and on which a collection of electrodes and a collection of fixation elements are mounted. The electrodes are in electrical contact with the electrical circuitry and the fixation elements increase the surface area of the biocompatible casing to reduce the likelihood that the biocompatible casing shifts after implantation.

15 Claims, 9 Drawing Sheets

(56) References Cited

U.S. PATENT DOCUMENTS

| | | |
|---|---|---|
| 5,865,842 A | 2/1999 | Knuth et al. |
| 6,434,431 B1 | 8/2002 | Camps et al. |
| 6,549,812 B1 | 4/2003 | Smits |
| 6,556,873 B1 | 4/2003 | Smits |
| 6,718,211 B2 | 4/2004 | Smits |
| 6,741,893 B2 | 5/2004 | Smits |
| 7,245,973 B2 | 7/2007 | Liu et al. |
| 7,463,934 B2 | 12/2008 | Tronnes et al. |
| 2002/0049485 A1 | 4/2002 | Smits |
| 2002/0065544 A1 | 5/2002 | Smits |
| 2003/0028232 A1 | 2/2003 | Camps et al. |
| 2003/0195600 A1 | 10/2003 | Tronnes et al. |
| 2004/0015204 A1 | 1/2004 | Whitehurst et al. |
| 2004/0015205 A1 | 1/2004 | Whitehurst et al. |
| 2004/0049240 A1 | 3/2004 | Gerber et al. |
| 2004/0162601 A1 | 8/2004 | Smits |
| 2004/0193228 A1 | 9/2004 | Gerber |
| 2004/0230282 A1 | 11/2004 | Cates et al. |
| 2005/0137671 A1 | 6/2005 | Liu et al. |
| 2005/0209653 A1 | 9/2005 | Herbert et al. |
| 2005/0234425 A1 | 10/2005 | Miller et al. |
| 2006/0036307 A1 | 2/2006 | Zarembo et al. |
| 2006/0095078 A1 | 5/2006 | Tronnes |
| 2006/0127158 A1 | 6/2006 | Olson et al. |
| 2006/0135999 A1 | 6/2006 | Bodner et al. |
| 2006/0184222 A1 | 8/2006 | Camps et al. |
| 2006/0265021 A1 | 11/2006 | Herbert et al. |
| 2007/0027512 A1 | 2/2007 | Chan et al. |
| 2007/0043414 A1 | 2/2007 | Fifer et al. |
| 2007/0073353 A1 * | 3/2007 | Rooney et al. .................. 607/36 |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088400 A1 | 4/2007 | Jacobson |
| 2007/0088405 A1 | 4/2007 | Jacobson |
| 2007/0088418 A1 | 4/2007 | Jacobson |
| 2007/0233216 A1 | 10/2007 | Liu et al. |
| 2008/0091255 A1 | 4/2008 | Caparso et al. |
| 2008/0183236 A1 | 7/2008 | Gerber |

FOREIGN PATENT DOCUMENTS

| | | |
|---|---|---|
| WO | 03086532 A1 | 10/2003 |
| WO | 04000416 A1 | 12/2003 |
| WO | 2006065394 A1 | 6/2006 |
| WO | 2007015907 A2 | 2/2007 |
| WO | 2007047681 A2 | 4/2007 |
| WO | 2007103262 | 9/2007 |
| WO | 2008045434 A2 | 4/2008 |

OTHER PUBLICATIONS

U.S. Appl. No. 12/361,432 Official Communication mailed Mar. 1, 2012.

International Preliminary Report on Patentability for International Application No. PCT/US2009/032231, mailed Aug. 12, 2010.

* cited by examiner

FIXATION OF IMPLANTABLE PULSE GENERATORS

CROSS-REFERENCE TO RELATED APPLICATIONS

The present application is a continuation of U.S. patent application Ser. No. 12/361,432 filed Jan. 28, 2009, which claims the benefit of U.S. Provisional Patent Application No. 61/024,115 filed Jan. 28, 2008, all of which are incorporated herein by reference in their entirety.

BACKGROUND

This disclosure relates to improving the fixation of implantable pulse generators.

Implantable pulse generators (IPG's) are implantable devices that deliver electrical pulses to cells or tissue. The electrical pulses can be delivered for therapeutic, functional, diagnostic, or other purposes.

SUMMARY

Systems and techniques for improving the fixation of implantable pulse generators are described. In one aspect, a device includes an implantable pulse generator. The implantable pulse generator can include electrical circuitry configured to generate an electrical pulse and a biocompatible casing that houses the electrical circuitry and on which a collection of electrodes and a collection of fixation elements are mounted. The electrodes are in electrical contact with the electrical circuitry and the fixation elements increase the surface area of the biocompatible casing to reduce the likelihood that the biocompatible casing shifts after implantation.

This and other aspects can include one or more of the following features. The fixation elements in the collection can be individually mounted directly to the biocompatible casing. The implantable pulse generator can include an adhesive to affix the fixation elements to the biocompatible casing and/or an implantable pulse generator fixation sleeve dimensioned to receive the biocompatible casing. The collection of fixation elements can be mounted to the implantable pulse generator fixation sleeve. The fixation sleeve can be secured or attached to the biocompatible casing.

The biocompatible casing can include a magnetically transparent portion and a magnetically non-transparent portion. The fixation elements can include a flexible polymeric material such as, e.g., silicone. The fixation elements can extend outwardly away from the biocompatible casing. The fixation elements can include spike fixation elements, rib fixation elements, trench fixation elements, and/or retractable fixation elements.

In another aspect, a device includes an implantable pulse generator. The implantable pulse generator can include a charging element configured to respond to a magnetic or electric field generated outside a body in which the implantable pulse generator is implanted and a biocompatible casing that houses the charging element and on which a collection of fixation elements are mounted. The fixation elements can increase the surface area of the biocompatible casing to reduce the likelihood that the biocompatible casing shifts after implantation.

This and other aspects can include one or more of the following features. The fixation elements in the collection can be individually mounted directly to the biocompatible casing. The implantable pulse generator can also include an implantable pulse generator fixation sleeve dimensioned to receive the biocompatible casing. The collection of fixation elements can be mounted to the implantable pulse generator fixation sleeve.

The biocompatible casing can include a magnetically transparent portion and a magnetically non-transparent portion. The magnetically transparent portion of the biocompatible casing can house the charging element. The implantable pulse generator can also include electrodes mounted to the biocompatible casing.

In another aspect, a device includes an implantable pulse generator. The implantable pulse generator can include electrical circuitry configured to generate an electrical pulse and a biocompatible casing that houses the electrical circuitry and on which a collection of electrodes and a collection of means for fixing the implantable pulse generator are mounted. The electrodes can be in electrical contact with the electrical circuitry. The means for fixing the implantable pulse generator can increase the surface area of the biocompatible casing to reduce the likelihood that the implantable pulse generator shifts after implantation.

In another aspect, a method includes inserting an implantable pulse generator into a body through a cannula of a closed surgical device, positioning the implantable pulse generator to deliver the electrical pulse to cells or tissue, and triggering deployment of one or more retractable fixation elements from the implantable pulse generator to reduce likelihood of shifting. The implantable pulse generator can include electrical circuitry configured to generate an electrical pulse and a biocompatible casing that houses the electrical circuitry and on which a collection of one or more retractable fixation elements are mounted.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
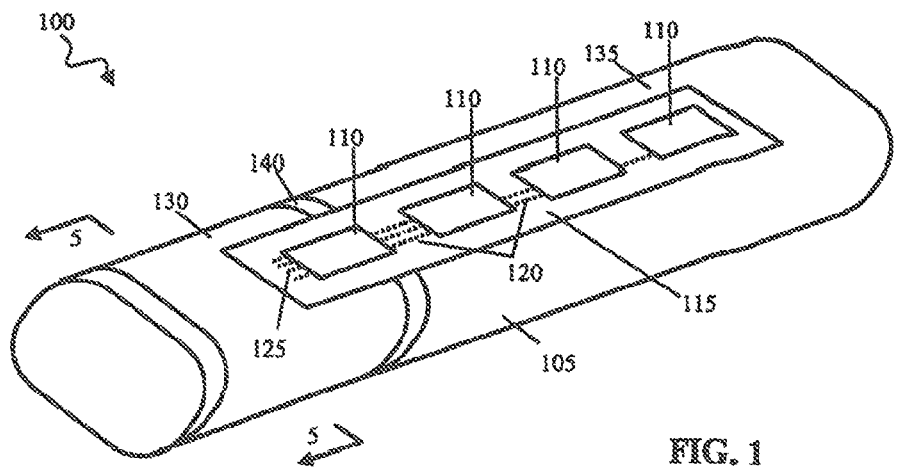
FIG. 1 is a diagrammatic view of an implantable pulse generator.
Figure 2:
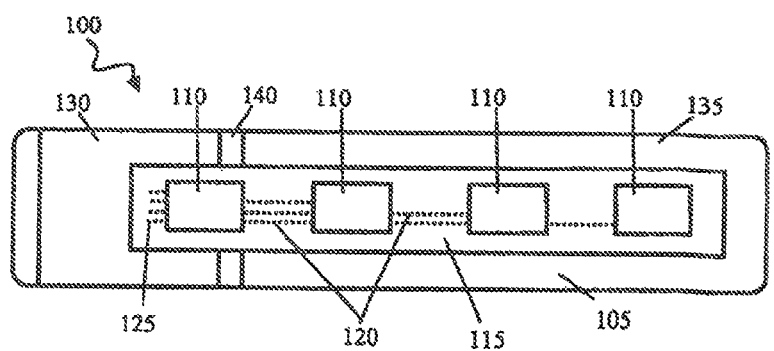
FIG. 2 is a view from above of the implantable pulse generator of FIG. 1.

FIG. 1 is a diagrammatic view and FIG. 2 is a view from above of an implantable pulse generator 100. Implantable pulse generator 100 is an implantable device that is adapted to deliver electrical pulses to cells or tissue. Implantable pulse generator 100 includes a biocompatible casing 105 on which a collection of electrodes 110 are mounted. Casing 105 is a generally elongate, hermetically-sealed member that encases power and control systems for the delivery of electrical pulses. Electrodes 110 are formed from a conductive material and are in electrical contact with power and control systems encased in casing 105.

In some implementations, two groups of four electrodes 110 can be positioned along a pair of contact strips 115 that are adhered to opposite sides of casing 105. Contact strips 115 can be formed of a polymeric material that encases a collection of conductive leads 120. At one or more positions 125, leads 120 can traverse casing 105 to place electrodes 110 in electrical contact with the power and control systems encased in casing 105.

Casing 105 can include a magnetically transparent portion 130 and a magnetically non-transparent portion 135. Magnetically transparent portion 130 is formed from a magnetically transparent material that does not substantially hinder the through transmission of a magnetic or electric field. For example, magnetically transparent portion 130 can be formed from a ceramic such as zirconia or alumina and/or from a polymeric material. Magnetically non-transparent portion 135 is formed from a material that is not magnetically transparent in that it hinders the through transmission of a magnetic or electric field. For example, magnetically non-transparent portion 135 can be formed from a metal, such as titanium. Magnetically transparent portion 130 and magnetically non-transparent portion 135 can be joined at a seam 140. Seam 140 can hermetically seal casing 105.

Figure 3:
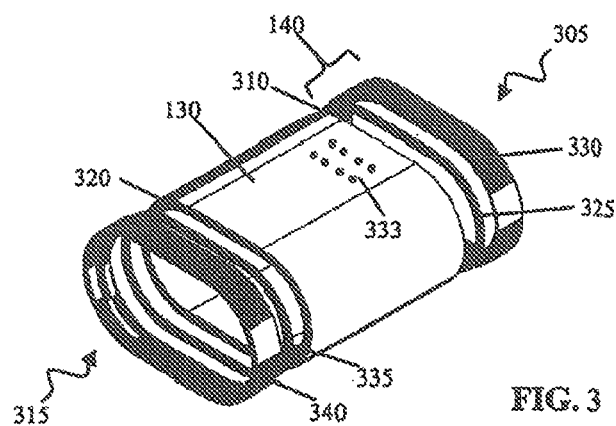
FIG. 3 shows one implementation of the joining of a magnetically transparent portion and a magnetically non-transparent portion of an implantable pulse generator.

FIG. 3 shows one implementation of the joining of portions 130, 135 at seam 140. In the illustrated implementation, magnetically transparent portion 130 is a zirconia cylinder with a rounded rectangular (e.g., a stadium) cross section. The cylinder of magnetically transparent portion 130 has a first open face 305 at a first end 310 and a second open face 315 at a second end 320. Seam 140 includes a rounded rectangular nickel braze ring 325 and a rounded rectangular titanium connector ring 330. Magnetically transparent portion 130 also includes a collection of holes 333 through which leads 120 can traverse casing 105, as discussed above.

During assembly, nickel braze ring 325 and titanium connector ring 330 are positioned around open face 305 at first end 310. This is then heated to braze connect magnetically transparent portion 130 and titanium connector ring 330. A comparable connection to, e.g., a cap (not shown) can be achieved using a second nickel braze ring 335 and a second titanium connector ring 340 at second end 320. Titanium connector ring 330 can be joined to the remainder of magnetically non-transparent portion 135 by, e.g., a compression or other fitting.

Figure 4:
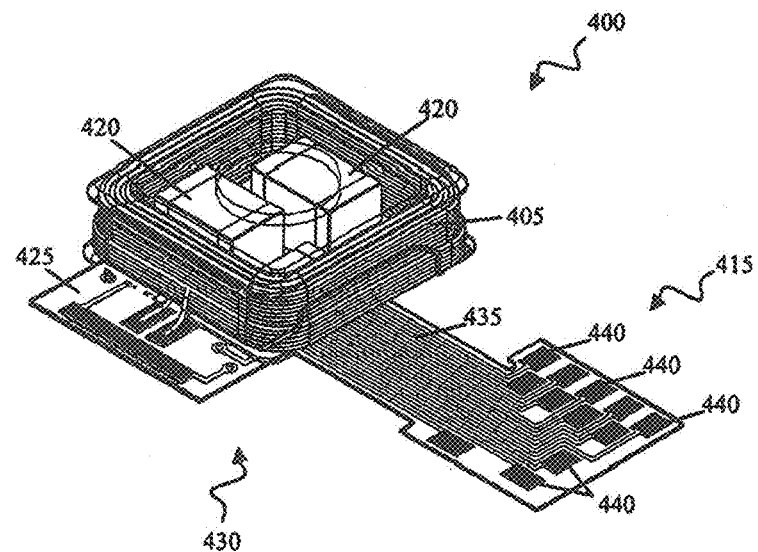
FIG. 4 is a diagrammatic view of a portion of the power and control systems of an implantable pulse generator.

FIG. 4 is a diagrammatic view of a portion 400 of the power and control systems that is dimensioned to fit within magnetically transparent portion 130 of casing 105. Portion 400 includes a charging coil 405, control electronics 410, and a one or more contact strips 415.

Charging coil 405 is a coiled conductor that can respond to a magnetic or electric field generated outside implantable pulse generator 100. For example, charging coil 405 can respond to a magnetic or electric field generated outside a body in which implantable pulse generator 100 is implanted. The motion of electrons in charging coil 405 under the influence of such a magnetic or electric field can be converted into potential energy and stored, e.g., at a rechargeable battery or other energy storage device in implantable pulse generator 100. Such an energy storage device can be a rechargeable lithium ion battery that is positioned in magnetically non-transparent portion 135 of implantable pulse generator 100.

Charging coil 405 surrounds a collection of capacitors 420. Capacitors 420 are mounted to a flexible-board circuit 425 along with other electrical components 430, such as a memory and an application specific integrated circuit. Together, capacitors 420, circuit 425, and components 430 form the electrical circuitry that manages the operation of implantable pulse generator 100, including the conversion of power from outside the body using charging coil 405 and the delivery of electrical pulses to cells or tissue using one or more electrodes 110. In some implementations, this electrical circuitry is programmable using an external (extracorporeal) wireless transmitter to change stimulation parameters, select and deselect electrodes for the delivery of electrical pulses, and the like.

Contact strip 415 is a flexible strip that encases a collection of leads 435 that are each electrically connected to a contact 440. With implantable pulse generator 100 in the assembled state, contacts 440 contact conductive leads 120 of contact strips 115 to form an electrical connection between portion 400 and electrodes 110 (FIG. 1). This electrical connection can be used to carry electrical pulses generated by the electrical circuitry of capacitors 420, circuit 425, and components 430 to electrodes 110. In some implementations, the electrical circuitry of capacitors 420, circuit 425, and components 430 can also use the electrical connection for sensing purposes. For example, one or more electrodes 110 can be used for potentiometric and/or amperometric measurements on a body in which implantable pulse generator 100. In some implementations, one or more contact strips can be used to form electrical connections between portion 400 and groups of electrodes 110 on opposite sides of casing 105.

Figure 5:
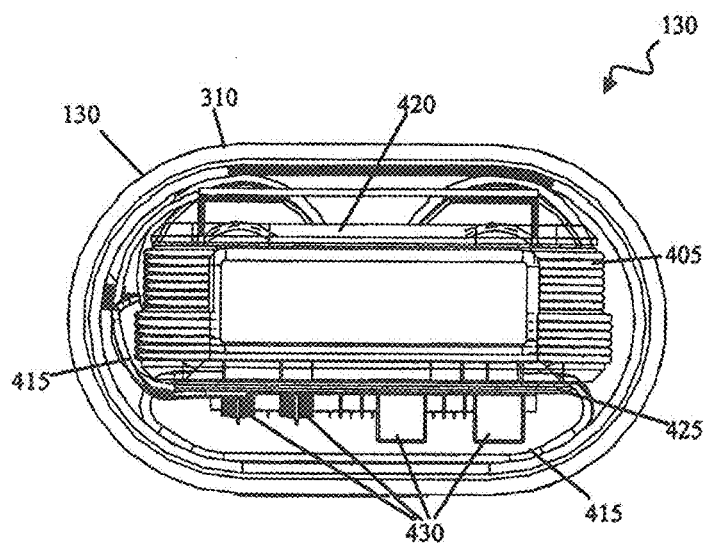
FIG. 5 is a side view of the assembly of the portion of the power and control systems of FIG. 4 into a magnetically transparent portion of an implantable pulse generator.

FIG. 5 is a side view of the assembly of portion 400 into magnetically transparent portion 130. As shown, charging coil 405 can be dimensioned to snugly fit into the interior of magnetically transparent portion 130. Contact strip 415 can be flexed to position contacts 440 adjacent holes 333 for connection with leads 120 across casing 105.

Figure 6:
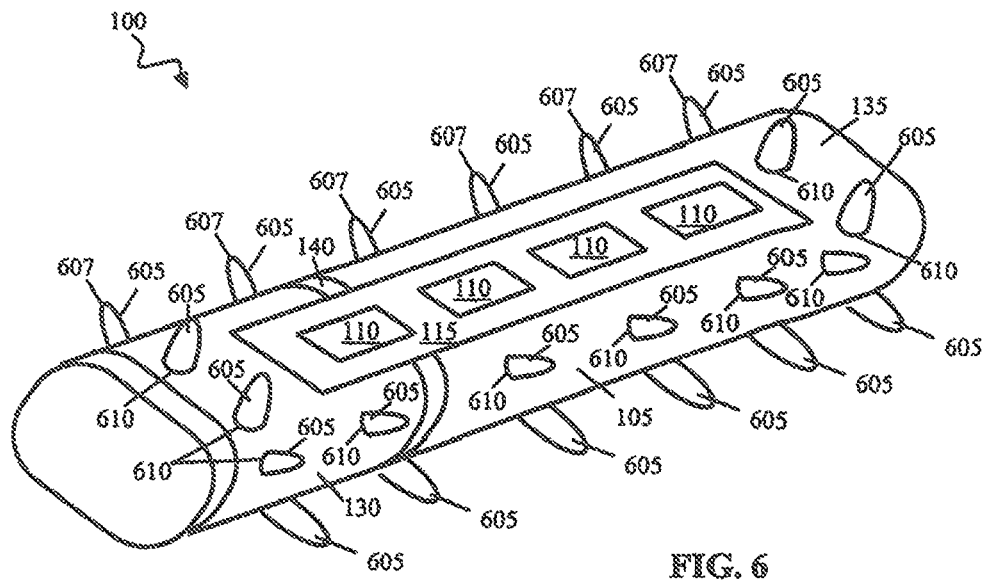
FIG. 6 is a diagrammatic view of an implantable pulse generator that includes a collection of spike fixation elements.

FIG. 6 is a diagrammatic view of an implantable pulse generator 100 that includes a collection of spike fixation elements 605. Spikes 605 are generally conical and resemble cones with rounded noses 607. Spikes 605 are discrete fixation elements in that each spike 605 is individually mounted directly to casing 105 at a site 610. Spikes 605 extend generally perpendicularly away from casing 105 and increase the surface area of casing 105. After implantation, tissue can surround spikes 605 and improve the fixation of implantable pulse generator 100 at the implantation site. The improved fixation can reduce the likelihood that casing 105 of implantable pulse generator 100 shifts (e.g., rotates or translates) after implantation.

In some implementations, spikes 605 can be designed with mechanical properties that are tailored to the mechanical behavior of the tissue in which implantable pulse generator 100 is to be implanted. For example, spikes 605 can have flexural moduli that allow spikes 605 to deflect in response to physiological movements of the tissue at an implantation site. For example, in soft tissue implantations, spikes 605 can be made from a flexible polymeric substance such as silicone composites with tailored moduli. Moduli can be tailored, e.g., by selection of the composition of the flexible polymeric substance and/or by the addition of glass or other fibers.

Spikes 605 can be individually mounted to both of magnetically transparent portion 130 and magnetically non-transparent portion 135 of casing 105. Spikes 605 can be excluded from the vicinity of contact strips 115 so that electrodes 110 can be positioned within range of the cells or tissue to which electrical pulses are to be delivered.

Spikes 605 can be mounted to casing 105 in a variety of ways. For example, spikes 605 can be cast directly on casing 105. As another example, spikes 600 can be affixed to casing 105 using an adhesive, after casting. In some implementations, the surface of one or more of magnetically transparent portion 130 and magnetically non-transparent portion 135 at sites 610 can be mechanically or chemically modified prior to mounting spikes 605. For example, sites 610 can be mechanically abraded, chemically roughened, or modified using surface active compounds prior to mounting.

Figure 7:
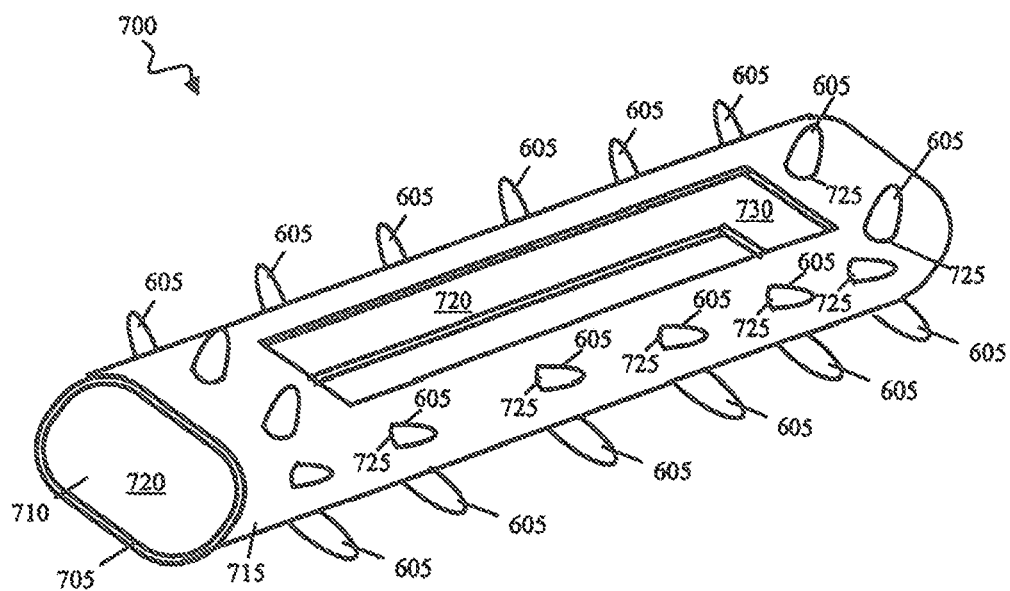
FIG. 7 is a diagrammatic view of an implantable pulse generator fixation sleeve that includes a collection of spike fixation elements.

FIG. 7 is a diagrammatic view of an implantable pulse generator fixation sleeve 700. Fixation sleeve 700 is a hollow, elongate member that includes a wall 705. Wall 705 has an inner surface 710 and an outer surface 715. Inner surface 710 defines the interior 720 of fixation sleeve 700. Interior 720 is dimensioned to snugly receive a casing of an implantable pulse generator, such as casing 105 of implantable pulse generator 100. In some implementations, fixation sleeve 700 can be secured to a casing of an implantable pulse generator, such as casing 105 of implantable pulse generator 100. For example, fixation sleeve 700 can be secured to casing 105 using one or more of a glue, an adhesive, a silicone, or a silicone composite. With an implantable pulse generator received in interior 720, any fixation elements on fixation sleeve 700 are, in effect, mounted on the implantable pulse generator.

A collection of spike fixation elements 605 are mounted to outer surface 715 of wall 705 at sites 725. Spikes 605 extend generally perpendicularly away from outer surface 715 of wall 705 and increase the outer surface area of fixation sleeve 700. Spikes 605 can be mounted to outer surface 715 of wall 705 in a variety of ways. For example, spikes 605 can be cast simultaneously with the remainder of fixation sleeve 700 and can be formed of the same material. For example, a fixation sleeve 700 with spikes 605 can be extrusion cast from a flexible polymeric substance such as silicone or silicone composites.

In some implementations, spikes 605 can be discrete elements that are affixed individually to outer surface 715 of wall 705 using an adhesive, e.g., after fixation sleeve 700 is cast. In some implementations, the outer surface 715 of wall 705 can be mechanically or chemically modified prior to mounting spikes 605.

Wall 705 of fixation sleeve 700 defines one or more cutout windows 730. Cutout windows 730 are generally rectangular-shaped cutouts along the length of fixation sleeve 700. Cutout windows 730 are positioned and dimensioned to correspond with the positioning and dimensions of electrodes on an implantable pulse generator when the implantable pulse generator is received in interior 720 of fixation sleeve 700. Such a positioning and dimensioning places the electrodes of a received implantable pulse generator in communication with surrounding tissue after implantation.

In some implementations, spikes 605 can be excluded from the vicinity of cutout windows 730 so that the electrodes of a received implantable pulse generator can be positioned within range of the cells or tissue to which electrical pulses are to be delivered.

Figure 8:
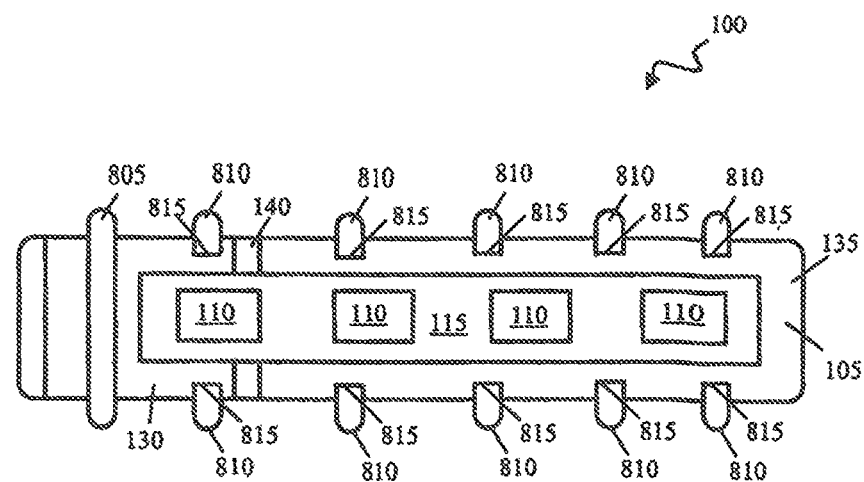
FIG. 8 is a view from above of an implantable pulse generator that includes a collection of rib fixation elements.

FIG. 8 is a view from above of an implantable pulse generator 100 that includes a collection of one or more circumferential rib fixation elements 805 and one or more segment rib fixation elements 810. Ribs 805, 810 are generally ridge-like fixation elements that resemble rings or ring segments. Ribs 805, 810 are discrete fixation elements in that each rib 805, 810 is individually mounted directly to casing 105. Ribs 805, 810 extend generally perpendicularly away from casing 105 and increase the surface area of casing 105. After implantation, tissue can surround ribs 805, 810 and improve the fixation of implantable pulse generator 100 at the implantation site. The improved fixation can reduce the likelihood that casing 105 of implantable pulse generator 100 shifts after implantation.

As shown, circumferential ribs 805 span the entirety of an outer circumferential surface of implantable pulse generator 100. Segment ribs 810 span a segment of the outer circumferential surface of implantable pulse generator 100 and terminate at locations 815. For example, segment ribs 810 can span segments between a pair of contact strips 115 on opposing sides of implantable pulse generator 100. In some implementations, segment ribs 810 can be excluded from the vicinity of contact strips 115 so that electrodes 110 can be positioned within range of the cells or tissue to which electrical pulses are to be delivered.

In some implementations, ribs 805, 810 can be designed with mechanical properties that are tailored to the mechanical behavior of the tissue in which implantable pulse generator 100 is to be implanted. For example, ribs 805, 810 can have flexural moduli that allow ribs 805, 810 to deflect in response to physiological movements of the tissue at an implantation site. For example, in soft tissue implantations, ribs 805, 810 can be made from a flexible polymeric substance such as silicone composites with tailored moduli.

Ribs 805, 810 can be mounted to casing 105 in a variety of ways. For example, ribs 805, 810 can be cast directly on casing 105. As another example, ribs 805, 810 can be affixed to casing 105 using an adhesive, after casting. In some implementations, the surface of casing can be mechanically or chemically modified prior to mounting ribs 805, 810. For example, casing 105 can be mechanically abraded, chemically roughened, or modified using surface active compounds prior to mounting.

Figure 9:
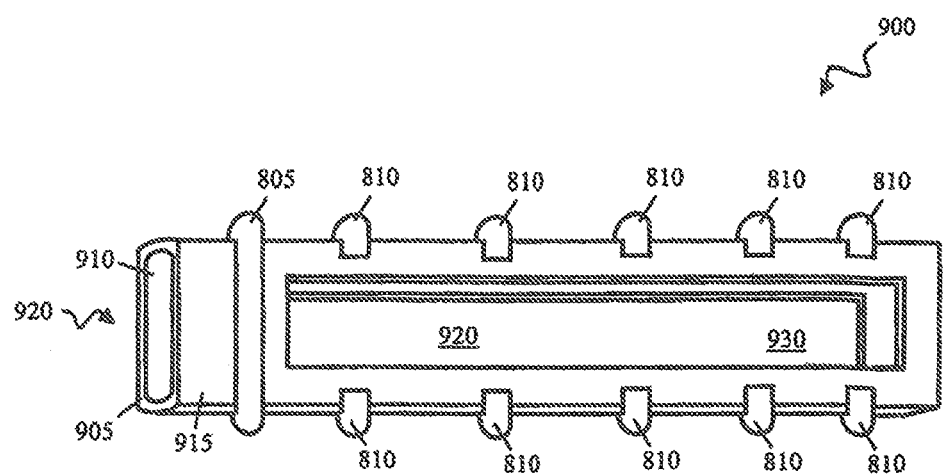
FIG. 9 is a diagrammatic view of an implantable pulse generator fixation sleeve that includes a collection of rib fixation elements.

FIG. 9 is a diagrammatic view of an implantable pulse generator fixation sleeve 900. Fixation sleeve 900 is a hollow, elongate member that includes a wall 905. Wall 905 has an inner surface 910 and an outer surface 915. Inner surface 910 defines the interior 920 of fixation sleeve 900. Interior 920 is dimensioned to snugly receive a casing of an implantable pulse generator, such as casing 105 of implantable pulse generator 100. With an implantable pulse generator received in interior 920, any fixation elements on fixation sleeve 900 are, in effect, mounted on the implantable pulse generator.

A collection of rib fixation elements 805, 810 are mounted to outer surface 915 of wall 905. Ribs 805, 810 extend generally perpendicularly away from outer surface 915 of wall 905 and increase the outer surface area of fixation sleeve 900. Ribs 805, 810 can be mounted to outer surface 915 of wall 905 in a variety of ways. For example, ribs 805, 810 can be cast simultaneously with the remainder of fixation sleeve 900 and can be formed of the same material. For example, a fixation sleeve 900 with ribs 805, 810 can be extrusion cast from a flexible polymeric substance such as silicone or silicone composites.

In some implementations, ribs 805, 810 can be discrete elements that are affixed individually to outer surface 915 of wall 905 using an adhesive, e.g., after fixation sleeve 900 is cast. In some implementations, the outer surface 915 of wall 905 can be mechanically or chemically modified prior to mounting ribs 805, 810.

Wall 905 of fixation sleeve 900 defines one or more cutout windows 930. Cutout windows 930 are generally rectangular-shaped cutouts along the length of fixation sleeve 900. Cutout windows 930 are positioned and dimensioned to correspond with the positioning and dimensions of electrodes on an implantable pulse generator when the implantable pulse generator is received in interior 920 of fixation sleeve 900. Such a positioning and dimensioning places the electrodes of a received implantable pulse generator in communication with surrounding tissue after implantation.

In some implementations, ribs 805, 810 can be excluded from the vicinity of cutout windows 930 so that the electrodes of a received implantable pulse generator can be positioned within range of the cells or tissue to which electrical pulses are to be delivered.

Figure 10:
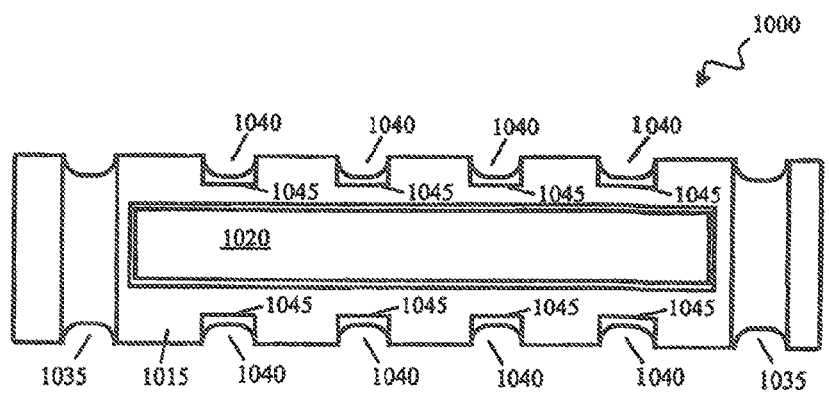
FIG. 10 is a view from above of an implantable pulse generator fixation sleeve that includes a collection of trench fixation elements.
Figure 11:
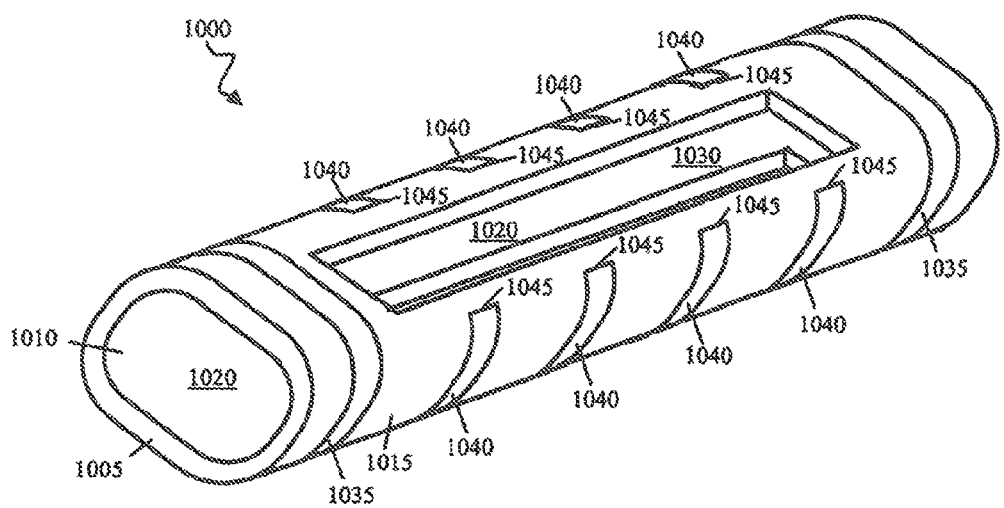
FIG. 11 is a diagrammatic view of the implantable pulse generator fixation sleeve of FIG. 10.

FIG. 10 is a view from above and FIG. 11 is a diagrammatic view of an implantable pulse generator fixation sleeve 1000. Fixation sleeve 1000 is a hollow, elongate member that includes a wall 1005. Wall 1005 has an inner surface 1010 and an outer surface 1015. Inner surface 1010 defines the interior 1020 of fixation sleeve 1000. Interior 1020 is dimensioned to snugly receive a casing of an implantable pulse generator, such as casing 105 of implantable pulse generator 100. With an implantable pulse generator received in interior 1020, any fixation elements on fixation sleeve 1000 are, in effect, mounted on the implantable pulse generator.

Wall 1005 defines a collection of one or more circumferential trench fixation elements 1035 and one or more segment trench fixation elements 1040. Trenches 1035, 1040 are generally elongate channels or depressions in wall 1005 and increase the surface area of wall 1005. After implantation, tissue can move into trenches 1035, 1040 and improve the fixation of implantable pulse generator 100 at the implantation site. The improved fixation can reduce the likelihood that casing 105 of an implantable pulse generator 100 shifts after implantation.

As shown, circumferential trenches 1035 span the entirety of an outer circumferential surface of fixation sleeve 1000. Segment trenches 1040 span a segment of the outer circumferential surface of fixation sleeve 1000 and terminate at locations 1045.

For example, segment trenches 1040 can span segments between one or more cutout windows 1030 defined in wall 1005 of fixation sleeve 1000. Cutout windows 1030 are generally rectangular-shaped cutouts along the length of fixation sleeve 1000. Cutout windows 1030 are positioned and dimensioned to correspond with the positioning and dimensions of electrodes on an implantable pulse generator when the implantable pulse generator is received in interior 1020 of fixation sleeve 1000. Such a positioning and dimensioning places the electrodes of a received implantable pulse generator in communication with surrounding cells or tissue after implantation.

Fixation sleeve 1000 can be designed with mechanical properties that are tailored to the mechanical behavior of the tissue in which an implantable pulse generator is to be implanted. For example, fixation sleeve 1000 can have flexural moduli that allow deflection in response to physiological movements of the tissue at an implantation site. For example, in soft tissue implantations, fixation sleeve 1000 can be made from a flexible polymeric substance such as silicone composites with tailored moduli.

Figure 12:
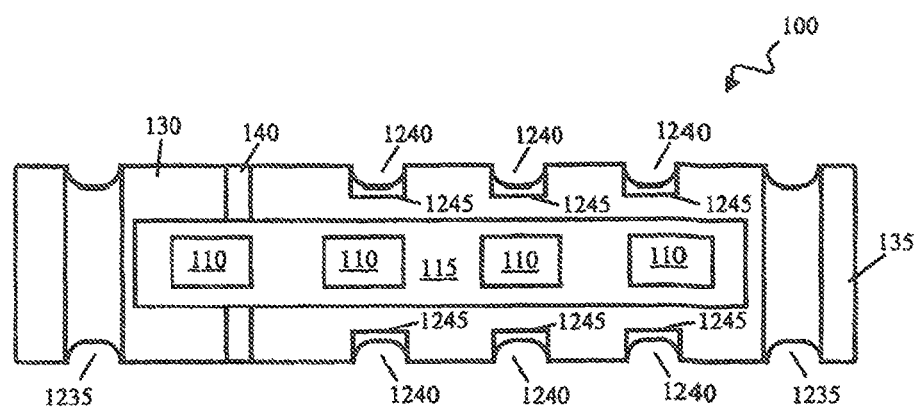
FIG. 12 is a view from above of an implantable pulse generator that includes a collection of circumferential trench fixation elements.
Figure 13:
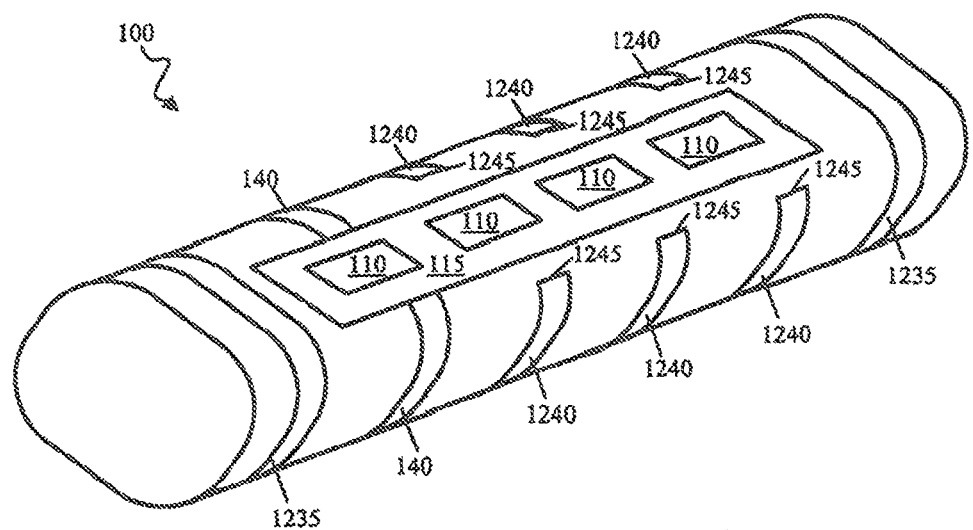
FIG. 13 is a diagrammatic view of the implantable pulse generator of FIG. 12.

FIG. 12 is a view from above and FIG. 13 is a diagrammatic view of an implantable pulse generator 100 that includes a collection of one or more circumferential trench fixation elements 1235 and one or more segment trench fixation elements 1240 in casing 105. Trenches 1235, 1240 are generally elongate channels or depressions in casing 105 and increase the surface area of casing 105. After implantation, tissue can move into trenches 1235, 1240 and improve the fixation of implantable pulse generator 100 at the implantation site. The improved fixation can reduce the likelihood that casing 105 of an implantable pulse generator 100 shifts after implantation.

Circumferential trenches 1235 span the entirety of an outer circumferential surface of implantable pulse generator 100. Segment trenches 1240 span a segment of the outer circumferential surface of implantable pulse generator 100 and terminate at locations 1245. For example, segment trenches 1240 can span segments between a pair of contact strips 115 on opposing sides of implantable pulse generator 100. In some implementations, segment trenches 1240 can be excluded from the vicinity of contact strips 115 so that electrodes 110 can be positioned within range of the cells or tissue to which electrical pulses are to be delivered.

Trenches 1235, 1240 can be formed in casing 105 in a variety of ways. For example, casing 105 can be cast, molded, machined, pressed, etched, or otherwise treated to form trenches 1235, 1240.

Figure 14:
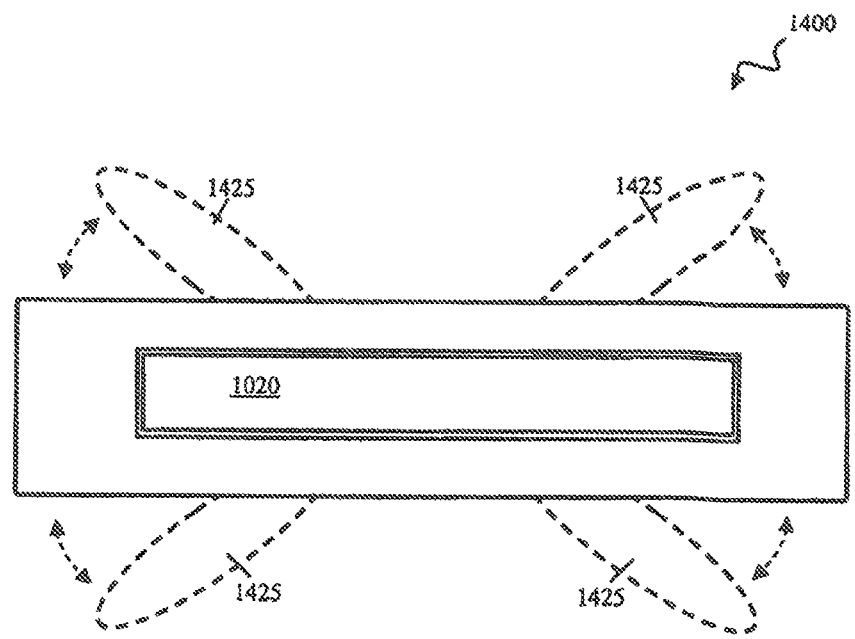
FIG. 14 is a view from above of an implantable pulse generator fixation sleeve that includes a collection of retractable fixation elements.
Figure 15:
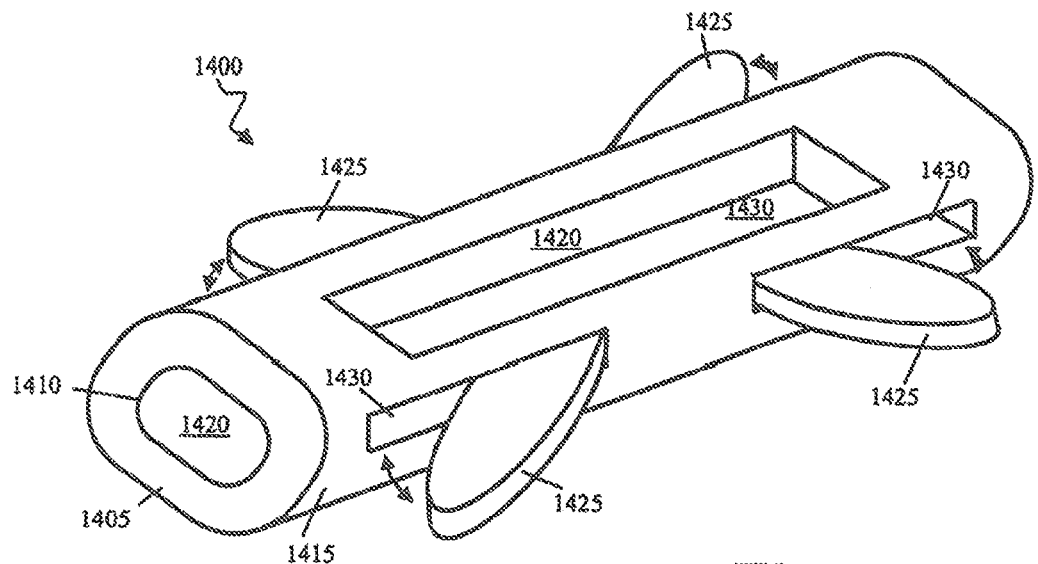
FIG. 15 is a diagrammatic view of the implantable pulse generator fixation sleeve of FIG. 14.

FIG. 14 is a view from above and FIG. 15 is a diagrammatic view of an implantable pulse generator fixation sleeve 1400. Fixation sleeve 1400 is a hollow, elongate member that includes a wall 1405. Wall 1405 has an inner surface 1410 and an outer surface 1415. Inner surface 1410 defines the interior 1420 of fixation sleeve 1400. Interior 1420 is dimensioned to snugly receive a casing of an implantable pulse generator, such as casing 105 of implantable pulse generator 100. With an implantable pulse generator received in interior 1420, any fixation elements on fixation sleeve 1400 are, in effect, mounted on the implantable pulse generator.

Fixation sleeve 1400 includes a collection of retractable fixation elements 1425. Retractable fixation elements 1425 are generally wing-shaped elements that can be moved between a position generally flush with an outer surface 1415 of wall 1405 of fixation sleeve 1400 and a position extending away from wall 1405 of fixation sleeve 1400. For example, in the illustrated implementation, retractable fixation elements 1425 can be housed in a collection of housings 1430 defined in wall 1405. Retractable fixation elements 1425 can be moved using a variety of different mechanisms. For example, retractable fixation elements 1425 can be spring loaded into fixation sleeve 1400.

In the deployed position extending away from fixation sleeve 1400, retractable fixation elements 1425 increase the surface area of fixation sleeve 1400. Once in the deployed position, tissue can surround retractable fixation elements 1425 and improve the fixation of implantable pulse generator 100 at the implantation site. The improved fixation can reduce the likelihood that casing 105 of an implantable pulse generator 100 shifts after implantation.

In operation, an implantable pulse generator can be inserted into fixation sleeve 1400 and implanted with the retractable fixation elements 1425 refracted, e.g., into housings 1430. In some cases, the implantable pulse generator/fixation sleeve 1400 assembly can be inserted through the cannula of a closed surgical device with retractable fixation elements 1425 retracted. Once in the body, the implantable pulse generator/fixation sleeve 1400 assembly can be positioned to deliver electrical stimulation to cells or tissue. Once the assembly is positioned properly, the deployment of retractable fixation elements 1425 can be triggered to reduce the likelihood that the assembly shifts. The deployment of retractable fixation elements 1425 can be triggered mechanically, electrically, or otherwise. For example, fixation sleeve 1400 can include a mechanical catch that can be manipulated to release spring-loaded retractable fixation elements 1425.

Figure 16:
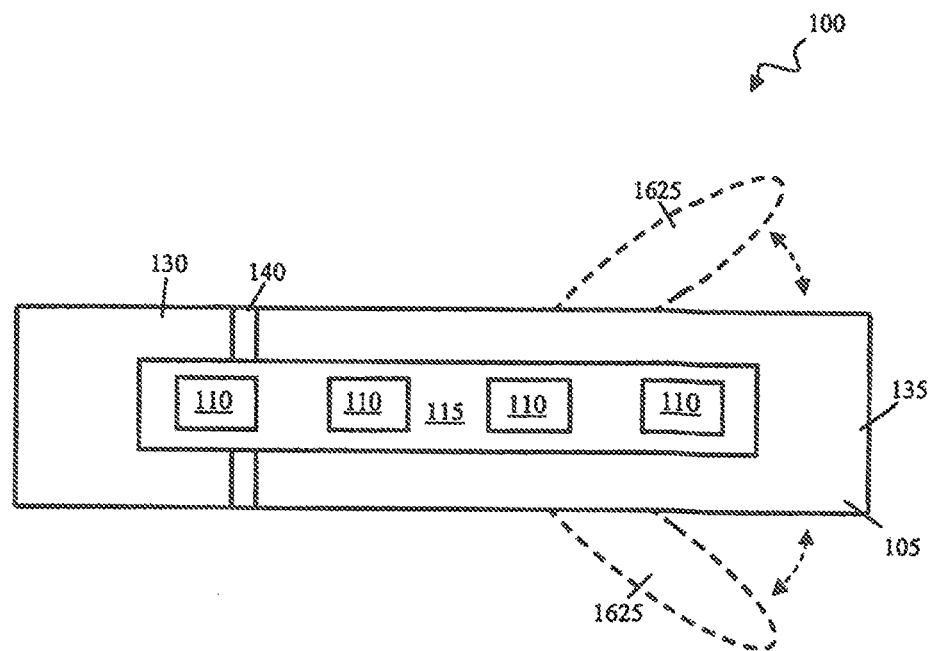
FIG. 16 is a view from above of an implantable pulse generator that includes a collection of retractable fixation elements.
Figure 17:
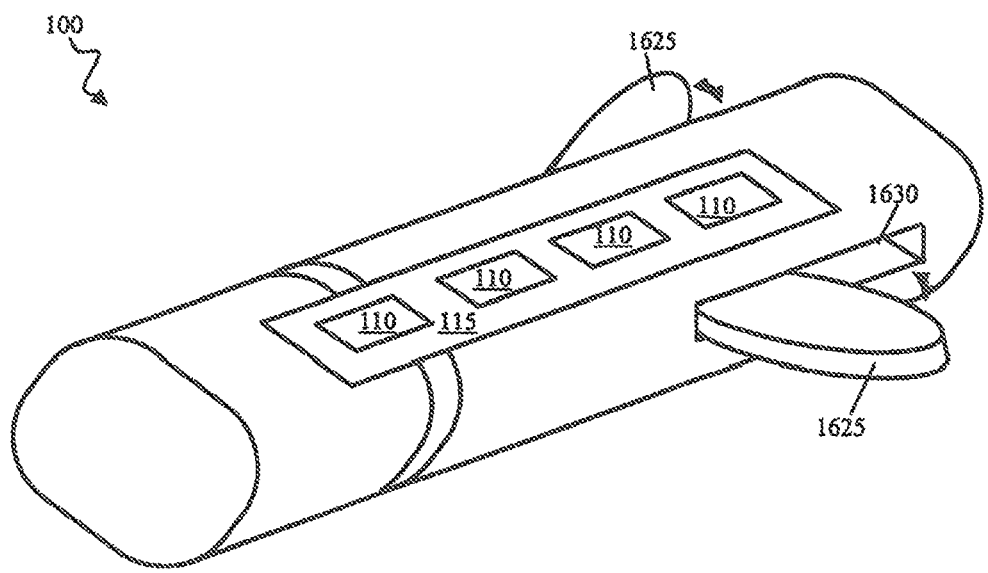
FIG. 17 is a diagrammatic view of the implantable pulse generator of FIG. 16.

FIG. 16 is a view from above and FIG. 17 is a diagrammatic view of an implantable pulse generator 100 that includes a collection of one or more retractable fixation elements 1625. Retractable fixation elements 1425 are generally wing-shaped elements that can be moved between a position generally flush with an outer surface of casing 105 and a position extending away from casing 105. For example, in the illustrated implementation, retractable fixation elements 1625 can be housed in a collection of housings 1630 defined in magnetically non-transparent portion 135 of casing 105. In some implementations, retractable fixation elements 1625 are spring loaded into housings 1630.

In the deployed position extending away from casing 105, retractable fixation elements 1625 increase the surface area of casing 105. Once in the deployed position, tissue can surround retractable fixation elements 1625 and improve the fixation of implantable pulse generator 100 at the implantation site. The improved fixation can reduce the likelihood that casing 105 of an implantable pulse generator 100 shifts after implantation.

In operation, implantable pulse generator 100 can be inserted into a body through the cannula of a closed surgical device with retractable fixation elements 1625 retracted. Once in the body, implantable pulse generator 100 can be positioned to deliver electrical stimulation to cells or tissue. Once implantable pulse generator 100 positioned properly, the deployment of retractable fixation elements 1625 can be triggered to reduce the likelihood that casing 105 of implantable pulse generator 100 shifts. The deployment of retractable fixation elements 1625 can be triggered mechanically, electrically, or otherwise. For example, a mechanical catch can be manipulated to release spring-loaded retractable fixation elements 1625 from housings 1630.

Figure 18:
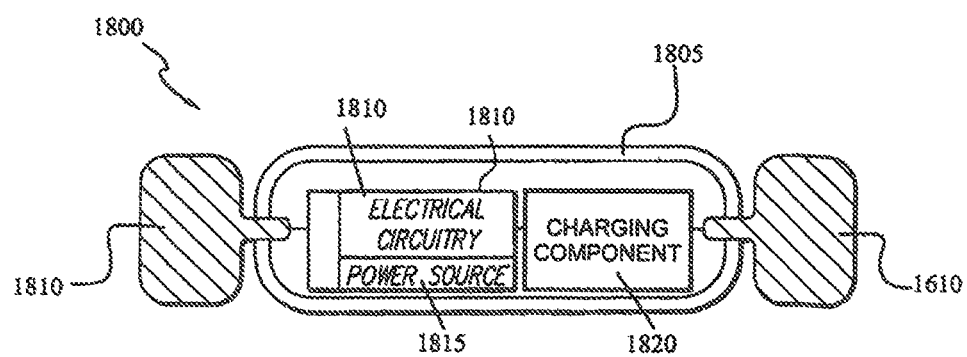
FIG. 18 is a schematic representation of another implantable pulse generator.

Although the implementations discussed above have been presented in the context of implantable pulse generators that generally resemble one another, the systems and techniques described herein can be used with other implantable pulse generator configurations. For example, FIG. 18 is a schematic representation of an implantable pulse generator 1800. Implantable pulse generator 1800 includes a generally cylindrical casing 1805. A pair of electrodes 1810 are mounted on opposite ends of casing 1805. Electrodes 1810 are in electrical contact with electrical circuitry 1810 that is housed in casing 1805. Energy for the operations performed by electrical circuitry 1810, including the delivery of electrical stimuli to cells or tissue over electrodes 1810, is supplied by a power source 1815. A charging component 1820 converts a magnetic or electric field from outside a body into potential energy to be stored at power source 1815. Both power source 1815 and charging component 1820 are also housed in casing 1805.

Implantable pulse generator 1800 itself, and a generally cylindrical fixation sleeve dimensioned to snugly receive casing 1805 of implantable pulse generator 1800, can be modified to include spike fixation elements, rib fixation elements, trench fixation elements, and/or retractable fixation elements.

A number of implementations have been described. Nevertheless, it will be understood that various modifications may be made. For example, fixation elements with different or random geometries can be used. Different geometries of fixation elements can be used in a single device. Accordingly, other implementations are within the scope of the following claims.

What is claimed and desired to be protected under United States Letters Patent:

1. An implantable pulse generator, comprising:
   electrical circuitry configured to generate an electrical pulse, and
   a biocompatible casing that houses the electrical circuitry and on which a plurality of electrodes and a plurality of fixation elements are mounted, wherein the plurality of fixation elements increase the surface area of the biocompatible casing to reduce the likelihood that the implantable pulse generator shifts after implantation, wherein the electrodes are in electrical contact with the electrical circuitry and the fixation elements are each a rib fixation element or a trench fixation element, wherein the plurality of fixation elements comprises at least two segment fixation elements, wherein each segment fixation element extends around, and spans, a segment of the outer circumference of the biocompatible casing, wherein the segment of the outer circumference is less than the entire outer circumference, wherein the at least two segment fixation elements comprises a first segment fixation element and a second segment fixation element disposed laterally opposite the first segment fixation element, wherein the plurality of electrodes comprises a first electrode that is disposed between laterally opposing ends of the first segment fixation element and the second segment fixation element.

2. The implantable pulse generator of claim 1, wherein each of the fixation elements is a rib fixation element.

3. The implantable pulse generator of claim 1, wherein each of the fixation elements is a trench fixation element.

4. The implantable pulse generator of claim 3, wherein each trench fixation element is a depression of a portion of the biocompatible casing.

5. The implantable pulse generator of claim 3, wherein each trench fixation element is an elongate channel in the biocompatible casing.

6. The implantable pulse generator of claim 1, wherein the plurality of fixation elements further comprises at least one circumferential fixation element, wherein each circumferential fixation element extends around the entire outer circumference of the casing.

7. The implantable pulse generator of claim 1, wherein the plurality of fixation elements further comprises two circumferential fixation elements, wherein each circumferential fixation element extends around the entire outer circumference of the easing and wherein each of the segment fixation elements is disposed between the two circumferential fixation elements.

8. The implantable pulse generator of claim 7, wherein the plurality of electrodes are disposed between the two circumferential fixation elements.

9. The implantable pulse generator of claim 1, wherein the at least two segment fixation elements comprises a third segment fixation element and a fourth segment fixation element laterally opposite the third segment fixation element, wherein the plurality of electrodes comprises a second electrode that is disposed between laterally opposing ends of the third segment fixation element and the fourth segment fixation element.

10. The implantable pulse generator of claim 1, wherein each of the plurality of electrodes is disposed between laterally opposing ends of two of the at least two segment fixation elements.

11. The implantable pulse generator of claim 1, wherein the biocompatible casing comprises a magnetically transparent portion and a magnetically non-transparent portion.

12. The implantable pulse generator of claim 11, further comprising a charging element, wherein the magnetically transparent portion of the biocompatible casing houses the charging element.

13. The implantable pulse generator of claim 1, wherein the biocompatible casing further comprises two contact strips upon which the plurality of electrodes are positioned, wherein the two contract strips are disposed on opposite sides of the biocompatible casing.

14. The implantable pulse generator of claim 13, wherein each of the at least two segment fixation elements is disposed circumferentially between the two contact strips.

15. The implantable pulse generator of claim 13, wherein each of the two contact strips is disposed between laterally opposing ends of at least two of the at least two segment fixation elements.

* * * * *